United States Patent [19]

Porter

[11] Patent Number: 4,457,907

[45] Date of Patent: Jul. 3, 1984

[54] COMPOSITION AND METHOD FOR PROTECTING A THERAPEUTIC DRUG

[75] Inventor: Garry L. Porter, Wichita, Kans.

[73] Assignee: Clear Lake Development Group, Wichita, Kans.

[21] Appl. No.: 405,510

[22] Filed: Aug. 5, 1982

[51] Int. Cl.$^3$ .................. A61K 9/30; A61K 31/00; A61K 9/22

[52] U.S. Cl. .................. 424/7.1; 424/10; 424/16; 424/31; 424/32; 424/36

[58] Field of Search .................. 424/7, 10, 16, 31–38

[56] References Cited

U.S. PATENT DOCUMENTS

| | | | |
|---|---|---|---|
| 874,310 | 12/1907 | Donard et al. | 424/36 |
| 1,335,488 | 3/1920 | Davis | 424/7.1 |
| 2,657,972 | 11/1953 | Woodward | 424/78 |
| 2,687,367 | 8/1954 | Burrin | 424/7.1 |
| 2,921,001 | 1/1960 | McDermott | 424/10 |
| 2,957,804 | 10/1960 | Shuyler | 424/10 |
| 2,996,431 | 8/1961 | Barry | 424/7.1 |
| 3,351,531 | 11/1967 | Noznick et al. | 424/36 |
| 3,629,390 | 12/1971 | Wentworth | 424/7.1 |
| 3,639,565 | 2/1972 | Prillig | 424/7.1 |
| 3,867,520 | 2/1975 | Mori et al. | 424/36 |
| 4,175,119 | 11/1979 | Porter | 424/10 |
| 4,230,687 | 10/1980 | Sair et al. | 424/36 |
| 4,291,016 | 9/1981 | Nougaret | 424/35 |
| 4,351,337 | 9/1982 | Sidman | 424/22 |

OTHER PUBLICATIONS

Hermandez et al., Chem. Abstracts 93 #199677z (1980) of Biopolymers (1980) 19(10); 1715–1721.

Kamei et al., Chem. Abstracts 87 #17676u (1977) of Chem. Pharm. Bull. (1976) 24(11): 2619–2623.

Rolfing et al., Chem. Abstracts 78 #148227k (1973) of Mol. Evol., 1972: 219–231.

Hennon et al., Chem. Abstracts 75 #64245g (1975) of Biochemie 1971 53(2): 215–223.

*Primary Examiner*—Shep K. Rose

[57] ABSTRACT

A therapeutic composition comprising a therapeutic drug that can cause undesirable effects on the pre-intestinal phases when contacting these phases, and an enteric coating surrounding the drug. A method for protecting a therapeutic drug including forming an enteric coating around the drug.

56 Claims, No Drawings

COMPOSITION AND METHOD FOR PROTECTING A THERAPEUTIC DRUG

BACKGROUND OF THE INVENTION

1. Field of the Invention

This invention is related to a therapeutic composition. More specifically, this invention provides for a therapeutic drug with an enteric coating and a method for protecting the therapeutic drug.

2. Description of Prior Art

Many pharmaceutical preparations that are administered orally pass through various gastrointestinal environments before reaching the area where their effectiveness is desired. In route to this effective location the preparation may be inactivated by salivary juices and/or the acid environment of the gastric lumen. The preparation may be irritating to the mucosal tissue along the way or it may be absorbed with undesired systemic effects.

These effects on the preparations have led me to posit that it would be most advantageous if some sort of coating of therapeutic materials could be selectively "triggered" at the desired action site in the gastrointestinal (GI) tract. Ideally, the material would be inactive in the GI tract before this site was reached and would be, in some fashion, inactivated from undesired action after the desired site was visited or the action accomplished.

In the past, the use of such things as polysaccharides or cellulose coatings have attempted to speak to this need. These coatings are, however, "activated" by their hydrophillic activity and the coating dissolves as a function of time and exposure to an H2O environment; that is, it is a non-specific response. In this age of increasingly potent (and at times toxic) materials, which are used for such things are chemotherapy, this non-specificity is a liability.

U.S. Pat. No. 874,310 discloses a pharmaceutical coating of maizin, a proteid, around a capsule. U.S. Pat. No. 3,004,893 teaches trypsin coated pills. The combination of trypsin and polyamino acid polymer coatings is disclosed in U.S. Pat. Nos. 3,167,485 and 3,331,814 for biodegradable sutures. These patents, nor any other prior art, teach my improved method and composition of this invention.

SUMMARY OF THE INVENTION

It is therefore an object of this invention to provide a composition coating and a method for protecting a therapeutic drug.

Still other objects will be apparent to those skilled in the art from the following description of this invention.

The foregoing objects are achieved according to the practice of this invention. Broadly, this invention comprises a therepeutic composition available for therapeutic action in the postgastric portion of the gastrointestinal tract of an animal or a human, wherein premature release of the composition in the pre-intestinal phases of the gastrointestinal tract can result in alteration of the composition or in undesirable effects on the pre-intestinal phases by the composition, including a therapeutic drug that can cause undesirable effects on the pre-intestinal phases when contacting these phases; and an enteric coating surrounding the therapeutic drug. The method for protecting a therapeutic drug from the effects of an oral, esophageal, and/or gastric environment found in an animal or human and then making the drug available in the postgastric portion of the gastro-intestinal tract includes the steps of forming an enteric coating around the drug. The coating is resistant to the gastric and pre-gastric environments while subject to chemical and/or enzymatical action in the post-gastric environment.

Thus, by the practice of this invention, there is provided a method and composition coating for protecting a therapeutic drug such that the drug is released in the small intestinal tract in an animal or human.

DETAILED DESCRIPTION OF THE INVENTION

This invention is a therapeutic composition which is available for therapeutic action in the postgastric portion of the gastrointestinal tract of an animal or a human, and wherein premature release of the therapeutic composition in the pre-intestinal phases of the gastrointestinal tract can result in alteration of the therapeutic composition or in undesirable effects on the pre-intestinal phases by the therapeutic composition. The therapeutic composition comprises a therapeutic drug that can cause the undesirable effects on the pre-intestinal phases when contacting these phases. An enteric coating is formed around the therapeutic drug. The process of coating is well known to those skilled in the art (e.g. pan coating, air-suspension coating, compression coating, etc) and controls the rate and site of the enteric coating release. Preferably, the coating has a thickness of from about 0.01 to about 1.0 mm. Each respective thickness should have a different color in order that one can readily determine what the thickness is. The coating can be a capsule to contain the drug.

In a preferred embodiment of the invention, the enteric coating is a polypeptide that is resistant to degradation in the gastric environment. More preferably, the polypeptide is selected from the group consisting of polyarginine, polylysine, or a mixture of polyarginine and polylysine.

The enteric coating of polyarginine, polylysine, or mixtures thereof, is immune to the acidic and enzymatic activities of the oral, esophageal and gastric environments and prevents the therapeutic drug from being released into these environments. The enteric coating, however, breaks down by the alkaline pH and selective proteolytic (enzymatic) action of trypsin which is an enzyme that is specific in clearing after every arginine and lysine residue in the polypeptide chain. Basic pH and trypsin are naturally present in the intestine and are essential for the destruction of the enteric polyarginine, polylysine, or polylysinylarginine coating. The substance—polyarginine, polylysine or polylysinylarginine—is not toxic and is available commercially as a dry powder. The material on enzymatic hydrolysis by trypsin yields the component amino acid(s) which is one of the required dietary ingredients of the normal human diet.

The by-product of the protective coating is a normal and desirable element of the diet, and therefore, cannot cause adverse effects, such as allergy, etc. The protective coating compound of this invention differs from prior art protective coating in that each prior art substance used (such as cellulose acetate phthalate, or maizin which is a substance containing proteins) for preparing a protective drug coating has failed to produce a truly protective coating. These substances have failed to withstand highly acidic and proteolytic(hydrolytic) environment of the stomach. The protective coating material proposed in this invention overcomes these drawbacks and is able to deliver the drug to a specific site in the digestive system; that is, the small intestine. Direct delivery of the drug to the small intestine is a highly desired feature for several therapeutic drugs since it avoids side effects and enhances the drug action.

Poly-L-arginine hydrochloride and sulfate salts are prepared from poly-L-ornithine in two sizes: 70 to 300 residues and 300 to 700 residues per chain. Similarly, poly-L-lysine hydrobromide is available in several sizes with varying number of lysine residues per polymer chain. Commercially available poly-L-arginine and poly-L-lysine salts produce viscous solutions, a necessary feature for creating a protective coating. A film of this material in desired thickness (i.e. from 0.01 to 1.0 mm) can be created around a given therapeutic drug by making use of the available technology for producing a stable protective coating.

The therapeutic drug may come in any size tablet, capsule, etc., such as 0.1, 0.5, 1, 5, 10, 25, 30, 50, 75, 100, 150, 200, 300, etc., mg. The drug may be any drug such as aspirin, vitamine, and medications which are psychotropic, anti-hypertensive, anti-seizure, amphetamine, anti-microbial, antibiotic, anti-fungal, anti-depressant, stimulants, anti-histamine, anti-alergy, phenothiazine, amines, monoamine oxidase inhibitors, anticarcinogens, analgesics, muscle relaxants, ergot preparations, anticholinergic, antiinflammatory, anti-gout preparations, soporfic, hormonal preparations, and appetite suppressants.

Vitamins may be any vitamin but is preferably B complex, folic acid derivatives, vitamin C, niacin, vitamin-mineral preparations, vitamin with iron, or combinations thereof. Also, the psychotropic medication may be any psychotropic medication but is preferably one selected from the group consisting of chlordiazepoxide, chlorazepote, clonazepam, chlorprothixene, and halazepam.

The anti-hypertensive drug may be any existing such drug, but is preferably one selected from the group consisting of quinethazone, ethacrynate, amiloride, trichlormethiazide, metolazone, prozosin.HCl, rescinnamine, polythiazide, tiamterene, captopril, bendroflumethazide-chlorthalidone minoxidil, methylclorthiazide, chlorthiazide, desiperidine, hydroflumethiazide, clonidine, hydralazine, hydrochlorthiazide, guanethidine, phentolamine, reserpine, metoprolol, furosemide, and cyclothiazide.

The preferred anti-siezure medication for this invention is one selected from the group consisting of metharbial, valproic acid, paramethadine, ethotoin, phenacemide, trimethadine, carbamazapine, phenytoin, and phensuximide. The amphetamine or amphetamine like compounds are preferably one selected from methamphetamine, phentermine, phenmetrazine, hydroflumethiazide, dextroamphetamine and benzphetamine.

The anti-microbial, or/and anti-biotic, or/and anti-fungal preparations are any of such drugs commercially available, however, in a preferred embodiment of the invention, such preparations are any selected from the group consisting of erythromycin, grise fulvin, lincomycin, sulfamethazole, sulfasalazine, sulfisoxazole, minocycline, chloramphenicol, nystatin, penicillen G and V, amoxicillen, tetracycline, dicloxacillen, nafcillen, ampicillen, chloroquine, hydrooxychloroquine, difampin, nitrofurantoin, methenamine, oxytetracycline, doxycycline, flucytosine, trimethoprim, carbicillen, bacampicillen, troleandomycen, cephradine, clindamycin, methacycline, nalidixic, metronidazole, oxacillen, methcillen, cloxacillen, cefadroxil, hetacillen, trimethoprim, cyclacillen, cinoxacin, cephalexin, ketoconazole, chlortetracycline, demeclocycline, neomycin, cephadroxil, piperazine, and pyrimethamine.

The antidepressant is preferably one selected from the group consisting of imipramine, maprotiline, trimipramine, amoxapine, nortryptylline, amitryptylline, protryptyline, and desipramine. The stimulant may be any stimulant but is preferably mathylphenidate.

The medication of our invention may also be any antihistamine and/or antiallergy preparation but is preferably one of the following: chlorpheniramine, theophylline, dimethindene, triprolidine, phenylpropanolamine, pyrobutamine, clemastine, amantadine, tripelemamine, diyphylline, cyproheptadine, doxylamine, guaifenesin, brompheniramine, diphenhydramine, oxtriphylline, carbinoxamine, dexbrompheniramine, azatadine, dexchlorpheniramine, pyribenzamine, trimeprazine, promethazine, and methidilazine.

The monoamine oxidase inhibitor drug is preferably either isoniazid, or phenelizine, or isocarboxazid. The amine unclassified is also preferably either ephedrine, quinine, quinidine, epinephrine, cyclobenzaprine, or pseudoephedrine.

The therapeutic drug of my invention may be an anticarcinogen such as one selected from the list consisting of mitotane, methotextrate, mitomycin, melphalen, chlorambucil, methotextrate, cyclophosphamide, 5-flourouracil, procarbazine, hydroxyurea, and tamoxifen.

The muscle relaxants of this invention may be one selected from orphendrine, methocarbanol, metaxaline, or chlorzoxazone, and the combination analgesic and muscle relaxant compound medication is preferably selected from the group consisting of: butorphanol, phenylbutazone, phenacetin, codiene, phenyltoloxamine, oxyphenylbutazone, hydrocodone, hydromorphone, propoxyphene, tolmetin, acetaminophen, zomepirac, levorphanol, naproxin, and pentazocaine.

Any of the following ergot preparations is preferred: ergotamine, ergoloid, or ergonovine. The anti-cholinergics may be oxyphenonium, procyclidine, biperiden, cycrimine, benztropine, homatropine, ethopropazine, glycopyrrolate, or hexocyclium.

In a preferred embodiment of the invention the antiinflammatory medication may be of the non-steroidal type such as ibuprofen, acetylsalicylic acid, oxyphenbutazone, paramethazone, sulindae, indomethacin, salsalate, sodiun D salicylate, or sodium adminobenzoate; or of the steroidal kind such as prednisone. The antigout preparation is preferably one from the group consisting of sulfinpyrazone, colchicine, and probenecid.

When the therapeutic drug is of the soporfic genesis, it is preferred that the soporfic is ethinamate, methaqualone, secobarbital, butabarbital, chloral hydrate, flurazepam, methyprylon, glutethiamide, ethchlorvynol, or restoril.

If the drug comes from a hormonal preparation, then it is preferably either norethindron, estrogens, methylprednisilone, danazol, stanazol, eradiol, progesterone, norgestrol, diethylstilbesterol, oxymetholone, triamcinalone, estradiol, dexamethasone, whole thyroid, or methyltestosterone.

The preferred appetite suppressant is one selected from the group consisting of phendimetrazine, mazindol, phentermine, and diethylpropian.

The following miscellaneous pharmaceutical preparations have also been found to be effective as a drug in this invention with respect to the purpose thereof: dextrothyroxine, sodium floride, papaverine, pancrealipase, tolbulamide, tolazamide, digutoxin, nadolol, propylthiouracil, methimazole, methyldopa, penicillamine, carbodopa and levodopa, mepenzolate, ioperamide, diphenidol, procainamide, potassium chloride, potassium iodide, chlorotrianisiseae, chlorpropamide, pyridostigmine, atenolol, pentaerythrital, methysergide, zinc sulfate, disulfiram, neostygmine, clofibrate, diphenoxylate, propantheline, clorterine, aminophyllin, allopurmal, carisoprodol, lanoxin, warfarin, cyclandelate, and dantrolene.

EXAMPLE I

Take any size of any of the therapeutic drug compositions mentioned in the foregoing paragraphs; form a 0.01 mm enteric coat of polyarginine, or polylysine, or polylysinylarginine, and ingest the enteric coated drug composition into a human or animal and find that the therapeutic drug by-passes the pre-intestinal phases of the gastrointestinal tract and is initially available in the postgastric portion of the same.

EXAMPLE II

Repeat example I but the surface of the therapeutic drug with an about 1.0 mm thickness of the enteric polymer coat and find similar results.

Thus, by the practice of this invention, there is provided a novel approach for delivery of therapeutic drugs directly to the small intestine. By delivering the drug directly to the small intestine, unwanted absorption in the oral, esophageal, and gastric environments to avoid the side effects in the body and the drug activity is enhanced.

While the present invention has been described herein with reference to particular embodiments thereof, a latitude of modification, various changes and substitutions are intended in the foregoing disclosure, and it will be appreciated that in some instance some features of the invention will be employed without a corresponding use of other features without departing from the scope of the invention as set forth.

I claim:

1. A therapeutic composition available for therapeutic action in the postgastric portion of the gastrointestinal tract of an animal or a human, wherein premature release of the composition in the pre-intestinal phases of the gastrointestinal tract can result in alteration of the composition or in undesirable effects on the pre-intestinal phases by the composition, comprising
   (a) a therapeutic drug that can cause undesirable effects on the pre-intestinal phases when contacting these phases; and
   (b) an enteric coating surrounding the therapeutic drug, said enteric coating is a polypeptide that is resistant to degradation in the gastric environment, and said coating has a thickness of from about 0.01 to about 1.0 mm, said polypeptide is selected from the group consisting of polyarginine, polylysine, or a mixture of polyarginine and polylysine.

2. The composition of claim 1 wherein said therapeutic drug is aspirin.

3. The composition of claim 1 wherein said therapeutic drug is a vitamin.

4. The composition of claim 1 wherein said therapeutic drug is a psychotropic medication.

5. The composition of claim 1 wherein said therapeutic drug is an anti-hypertensive medication.

6. The composition of claim 1 wherein said therapeutic drug is an anti-seizure medication.

7. The composition of claim 1 wherein said therapeutic drug is an amphetamine medication.

8. The composition of claim 1 wherein said therapeutic drug is an anti-microbial medication.

9. The composition of claim 1 wherein said therapeutic drug is an antibiotic medication.

10. The composition of claim 1 wherein said therapeutic drug is an anti-fungal medication.

11. The composition of claim 1 wherein said therapeutic drug is an anti-depressant medication.

12. The composition of claim 1 wherein said therapeutic drug is a stimulant medication.

13. The composition of claim 1 wherein said therapeutic drug is an antihistamine medication.

14. The composition of claim 1 wherein said therapeutic drug is an antiallergy medication.

15. The composition of claim 1 wherein said therapeutic drug is a phenothiazine medication.

16. The composition of claim 1 wherein said therapeutic drug is an amine medication.

17. The composition of claim 1 wherein said therapeutic drug is a monoamine oxidase inhibitor medication.

18. The composition of claim 1 wherein said therapeutic drug is an anticarcinogen medication.

19. The composition of claim 1 wherein said therapeutic drug is an analgesic medication.

20. The composition of claim 1 wherein said therapeutic drug is a muscle relaxant medication.

21. The composition of claim 1 wherein said therapeutic drug is an ergot preparation medication.

22. The composition of claim 1 wherein said therapeutic drug is an anticholinergic medication.

23. The composition of claim 1 wherein said therapeutic drug is an antiinflammatory medication.

24. The composition of claim 1 wherein said therapeutic drug is an antigout preparation medication.

25. The composition of claim 1 wherein said therapeutic drug is a soporfic medication.

26. The composition of claim 1 wherein said therapeutic drug is a hormonal preparation medication.

27. The composition of claim 1 wherein said therapeutic drug is an appetite suppressant medication.

28. A method for protecting a therapeutic drug from the effects of an oral, esophageal, and/or gastric environment found in an animal or human and then making the drug available in the postgastric portion of the gastro-intestinal tract, comprising the steps of: forming an enteric coating around the drug, said coating being resistant to the gastric and pre-gastric environments and being subject to chemical and/or enzymatical action in the postgastric environment, said forming of an enteric coating is with a polypeptide which is resistant to gastric and pregastric environment and selected from the group consisting of polyarginine, polylysine, or a mixture of polyarginine and polylysine, said coating having a thickness of from about 0.01 to about 1.0 mm.

29. The method of claim 28 wherein said therapeutic drug is aspirin.

30. The method of claim 28 wherein said therapeutic drug is a vitamin.

31. The method of claim 28 wherein said therapeutic drrug is a psychotropic medication.

32. The method of claim 28 wherein said therapeutic drug is an anti-hypertensive medication.

33. The method of claim 28 wherein said therapeutic drug is an anti-seizure medication.

34. The method of claim 28 wherein said therapeutic drug is an amphetamine medication.

35. The method of claim 28 wherein said therapeutic drug is an anti-microbial medication.

36. The method of claim 28 wherein said therapeutic drug is an antibiotic medication.

37. The method of claim 28 wherein said therapeutic drug is an anti-fungal medication.

38. The method of claim 28 wherein said therapeutic drug is an anti-depressant medication.

39. The method of claim 28 wherein said therapeutic drug is a stimulant medication.

40. The method of claim 28 wherein said therapeutic drug is an antihistamine medication.

41. The method of claim 28 wherein said therapeutic drug is an antiallergy medication.

42. The method of claim 28 wherein said therapeutic drug is a phenothrazine medication.

43. The method of claim 28 wherein said therapeutic drug is an amine medication.

44. The method of claim 28 wherein said therapeutic drug is a monoamine oxidase inhibitor medication.

45. The method of claim 28 wherein said therapeutic drug is an anticarcinogen medication.

46. The method of claim 28 wherein said therapeutic drug is an analgesic medication.

47. The method of claim 28 wherein said therapeutic drug is a muscle relaxant medication.

48. The method of claim 28 wherein said therapeutic drug is an ergot preparation medication.

49. The method of claim 28 wherein said therapeutic drug is an anticholinergic medication.

50. The method of claim 28 wherein said therapeutic drug is an antiinflammatory medication.

51. The method of claim 28 wherein said therapeutic drug is an antigout preparation medication.

52. The method of claim 28 wherein said therapeutic drug is a soporfic medication.

53. The method of claim 28 wherein said therapeutic drug is a hormonal preparation medication.

54. The method of claim 28 wherein said therapeutic drug is an appetite suppressant medication.

55. The composition of claim 1 wherein said enteric coating comprises a certain color for a certain thickness in order to readily ascertain the enteric coating thickness.

56. The method of claim 28 additionally comprising coloring each coating thickness a different color in order that the user can readily determine the coating thickness.

* * * * *

UNITED STATES PATENT AND TRADEMARK OFFICE
Certificate

Patent No. 4,457,907 Patented August 5, 1982

Gary L. Porter

Application having been made by Gary L. Porter, the inventor named in the patent above identified, and Clear Lake Development Group, the assignee, for the issuance of a certificate under the provisions of Title 35, Section 256, of the United States Code, adding the name of Ram P. Singhal as a joint inventor, and a showing and proof of facts satisfying the requirements of the said section having been submitted, it is this 16th day of Oct. 1984, certified that the name of the said Ram P. Singhal is hereby added to the said patent as a joint inventor with the said Gary L. Porter.

Fred W. Sherling,
*Associate Solicitor.*